United States Patent

Metzger et al.

[11] Patent Number: 6,040,443
[45] Date of Patent: Mar. 21, 2000

[54] PROCESS FOR THE PRODUCTION OF BENZOXAZINONES

[75] Inventors: Georges Metzger, Moernach, France; Dieter Reinehr, Kandern, Germany; Serge Hauger, Ransbach-le-Bas, France

[73] Assignee: Ciba Specialty Chemicals Corporation, Tarrytown, N.Y.

[21] Appl. No.: 09/119,300

[22] Filed: Jul. 20, 1998

[30] Foreign Application Priority Data

Jul. 22, 1997 [GB] United Kingdom ............ 9715312

[51] Int. Cl.⁷ ................................................ C07D 265/02
[52] U.S. Cl. .................................... 544/90; 544/92
[58] Field of Search ............................ 544/90, 92

[56] References Cited

U.S. PATENT DOCUMENTS 3,544,566  12/1970  Brunetti .................................. 260/244

OTHER PUBLICATIONS

Brunetti et al., "Die Synthese von Asymmetrisch Substituierten Omicron–Hydroxyphenyl–Sigma–Triazinen" Helvetica Chimica Acta, vol. 55, No. 1, (1972), pp. 1566–1595.

*Primary Examiner*—Richard L. Raymond
*Attorney, Agent, or Firm*—Kevin T. Mansfield

[57] ABSTRACT

There is described a process for the production of a 1,3-benzoxazin-4-one having the formula:

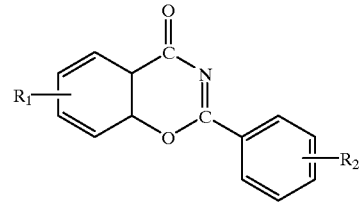

(1)

in which $R_1$ and $R_2$, independently, are hydrogen, cyano, halogen, nitro, $C_1$–$C_{20}$alkyl, O—$C_1$–$C_{20}$alkyl, phenyl, NH—CO—$C_1$–$C_{20}$alkyl, $N(R_3)_2$, $SO_2N(R_3)_2$, $COOR_3$ or $CON(R_3)_2$ in which $R_3$ is hydrogen, cyano, halogen, nitro, $C_1$–$C_{20}$alkyl, O—$C_1$–$C_{20}$alkyl, phenyl or NH—CO—$C_1$–$C_{20}$alkyl, comprising reacting, at elevated temperature, 1 molar equivalent of an o-hydroxybenzamide of formula:

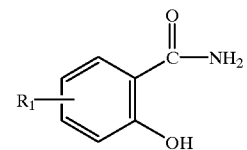

(2)

in which $R_1$ has its previous significance, with 2 to 6 molar equivalents of a benzoyl chloride of formula:

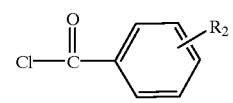

(3)

in which $R_2$ has its previous significance. The 1,3-benzoxazin-4-ones having the formula (1) so obtained are important intermediates for the production of triazine compounds having excellent absorption spectrum characteristics and good resistance to exposure to UV light.

10 Claims, No Drawings

PROCESS FOR THE PRODUCTION OF BENZOXAZINONES

The present invention relates to a process for the production of 1,3-benzoxazin-4-ones which are important intermediates for the production of triazine compounds having excellent absorption spectrum characteristics and good resistance to exposure to UV light.

In U.S. Pat. No. 3,544,566 there is described a process for the production of areno-oxazinones comprising heating a mixture of a) a compound R—CO—X in which X is chlorine or bromine and R is the radical of a carbocyclic aromatic or of a heterocyclic aromatic ring system having from one to three 5- or 6-membered rings, which system contains at least one ring free from nitrogen atoms as ring members and a carbon atom of which is linked to the CO group in the above formula, and b) an o-hydroxy-aryl-carboxylic acid amide of the formula A(OH)—CO—NH$_2$ in which A is the divalent radical of a carboxylic aromatic ring system havng from one to at most three 6-membered rings. The heating is conducted at 60 to 230° C. and hydrogen halide and water formed during the ensuing reaction are continuously removed from the mixture. There is obtained, as condensation product, a compound of the formula:

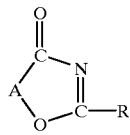

in which A and R have their previous significance.

The disclosed process uses 0.8 to 1.5, preferably about 1.1 equivalents of the compound R—CO—X per eqivalent of the o-hydroxy-aryl-carboxylic acid amide of the formula A(OH)—CO—NH$_2$. The yields obtained in the disclosed process, however, are variable and can fall as low as 17%. The disclosed reaction is preferably conducted in the presence of an organic solvent, especially xylene, in order to facilitate the removal of water as an an azeotropic mixture with the solvent. In the only specific Example in U.S. Pat. No. 3,544,566 in which the reaction was conducted in the absence of solvent, only moderate yield (41.5%) of the desired oxazinone was obtained.

It has now been found that consistently high yields of 1,3-benzoxazin-4-ones can be obtained, in a solvent-free process, using shorter reaction times and smaller reaction volumes than those applied in the process of U.S. Pat. No. 3,544,566, by the reaction of 2 to 6 molar equivalents of a benzoyl chloride with 1 molar equivalent of an o-hydroxybenzamide.

Accordingly, the present invention provides a process for the production of a 1,3-benzoxazin-4-one having the formula:

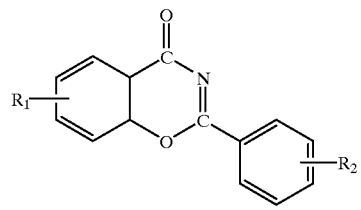

(1)

in which $R_1$ and $R_2$, independently, are hydrogen, cyano, halogen, nitro, $C_1$–$C_{20}$alkyl, O—$C_1$–$C_{20}$alkyl, phenyl, NH—CO—$C_1$–$C_{20}$alkyl, $N(R_1)_2$, $SO_2N(R_1)_2$, $COOR_1$ or $CON(R_1)_2$ in which $R_1$ has its previous significance, comprising reacting, at elevated temperature, 1 molar equivalent of an o-hydroxybenzamide of formula:

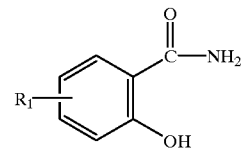

(2)

in which $R_1$ has its previous significance, with 2 to 6 molar equivalents of a benzoyl chloride of formula:

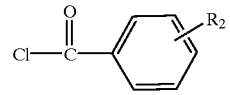

(3)

in which $R_2$ has its previous significance.

When $R_1$ and/or $R_2$ is halogen, such halogen substituents are fluorine, bromine, iodine or, especially, chlorine substituents.

$C_1$–$C_{20}$alkyl groups $R_1$ and/or $R_2$ may be branched or unbranched such as methyl, ethyl, n-propyl, isopropyl, n-butyl, sec-butyl, isobutyl, t-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, n-nonyl, n-decyl, n-undecyl, 1-methylundecyl, n-dodecyl, 1,1,3,3,5,5-hexamethylhexyl, n-tridecyl, n-tetradecyl, n-pentadecyl, n-hexadecyl, n-heptadecyl, n-octadecyl and n-eicosyl but are preferably methyl or ethyl.

O—$C_1$–$C_{20}$alkyl groups $R_1$ and/or $R_2$ may be branched or unbranched such as methoxy, ethoxy, n-propoxy, isopropoxy, n-butoxy, sec-butoxy, isobutoxy, t-butoxy, 2-ethylbutoxy, n-pentoxy, isopentoxy, 1-methylpentoxy, 1,3-dimethylbutoxy, n-hexoxy, 1-methylhexoxy, n-heptoxy, isoheptoxy, 1,1,3,3-tetramethylbutoxy, 1-methylheptoxy, 3-methylheptoxy, n-octoxy, 2-ethylhexoxy, 1,1,3-trimethylhexoxy, 1,1,3,3-tetramethylpentoxy, n-nonoxy, n-decoxy, n-undecoxy, 1-methylundecoxy, n-dodecoxy, 1,1,3,3,5,5-hexamethylhexoxy, n-tridecoxy, n-tetradecoxy, n-pentadecoxy, n-hexadecoxy, n-heptadecoxy, n-octadecoxy and n-eicosoxy, preferably methoxy, ethoxy or propoxy groups, especially methoxy groups.

Preferably $R_1$ and $R_2$, independently, are hydrogen, cyano, chloro, nitro, $C_1$–$C_4$alkyl, $C_1$–$C_4$alkoxy, NH—CO—

$C_1$–$C_4$alkyl, $N(C_1$–$C_4$alkyl$)_2$, $SO_2N(C_1$–$C_4$alkyl$)_2$, CON$(C_1$–$C_4$alkyl$)_2$, CO—OC$_1$—C$_4$alkyl or phenyl.

The process according to the present invention is conducted at an elevated temperature preferably at a temperature ranging from 50° C. to 180° C., especially preferably at a temperature ranging from 100° C. to 160° C. The process is conveniently carried out over a reaction time within the range of from 1 to 24 hours, preferably within the range of from 2 to 5 hours.

The amount of the reactant of formula (3) used according to the process of the present invention is in excess of the stoichiometric amount required for complete reaction of the reactant of formula (2). Preferably, the molar ratio of the reactant of formula (3) to the reactant of formula (2) ranges from 2:1 to 6:1, more preferably from 2.01:1 to 4:1, especially from 2.01 to 2.5:1.

Normally and preferably, the process of the present invention is conducted by heating the reaction mixture, in the absence of any external solvent, until a melt is formed. In less preferred instances in which it is desired to conduct the reaction at a temperature below that necessary to form a melt, then an external solvent such as dimethylacetamide may be added in order to form a homogeneous liquid reaction mixture.

Examples of reactants of formula (2) include 2-hydroxy-, 2-hydroxy-4cyano-, 2-hydroxy4-chloro-, 2-hydroxy-5-nitro-, 2-hydroxy-4-methyl-, 2-hydroxy-5-ethyl-, 2-hydroxy-4-methoxy-, 2-hydroxy-4-ethoxy-, 2-hydroxy-4-methoxycarbonylamino-, 2-hydroxy-5-butoxycarbonylamino-, 2-hydroxy-4-dimethylamino-, 2-hydroxy-5-diethylamino-, 2-hydroxy-dimethylaminosulfonyl-, 2-hydroxy-dibutylaminosulfonyl-, 2-hydroxy-dimethylaminocarbonyl-, 2-hydroxy-5-dipropylaminocarbonyl-, 2-hydroxy-4-methoxycarbonyl-, 2-hydroxy-3-ethoxycarbonyl- and 2-hydroxy-4-phenyl-benzamide.

Examples of reactants of formula (3) include benzoic acid chloride, 4-cyano-, 4-chloro-, 5-nitro-, 4-methyl-, 5-ethyl-, 4-methoxy-, 4-ethoxy-, 4-methoxycarbonylamino-, 5-butoxycarbonylamino-, 4-dimethylamino-, 5-diethylamino-, 4-dimethylaminosulfonyl-, 4-dibutylaminosulfonyl-, dimethylaminocarbonyl-, 5-dipropylaminocarbonyl-, 4-methoxycarbonyl-, 3-ethoxycarbonyl- and 4-phenyl-benzoic acid chloride.

The compound of formula (1) is obtained in high yields of up to 95% according to the process of the present invention. The process is normally conducted in the absence of any added solvent which greatly simplifies the operation of the process and renders it more economically and environmentally acceptable. Benzoic acid produced as a by-product of the process of the present invention can be recovered.

The following Examples further illustrates the present invention.

EXAMPLE 1

6.85 g (50 mmol) of salicylic acid amide are added, dropwise, to 11.5 ml of benzoyl chloride and the mixture is heated to 170° C. The mixture is then stirred for 30 minutes at this temperature. During this time, the salicylic acid dissolves to produce, on cooling, a honey-like mass containing 2-phenyl-4H-benzoxazin-4-one in quantitative yield. The 2-phenyl-4H-benzoxazin-4-one so obtained is then used to produce a triazine compound in the following manner.

12.6 g (53 mmol) of biphenylamidine hydrochloride are added to 100 ml of methanol. The reaction mass (50 mmol) containing 2-phenyl4H-benzoxazin-4-one, without isolation or purification, is added, and then 18.0 g (100 mmol) of a 30% solution of sodium hydroxide in methanol are added, with vigorous stirring. The compound 2-biphenyl-4-hydroxyphenyl-1,3,5-triazine is precipitated out from the reaction mixture and is stirred for 1 hour at 70° C., filtered off with suction and washed. The yield of 2-biphenyl-4-hydroxyphenyl-1,3,5-triazine having m.pt. of 248–249° C. is 16.75 g (41.8 mmol=83.6%).

Elemental analysis of the 2-biphenylthydroxyphenyl-1,3,5-triazine so obtained and having the empirical formula $C_{27}H_{19}N_3O$ gives:

Req.% C 80.78; H 4.77; N 10.47. Found % C 80.88; H 4.70; N 10.49.

EXAMPLE 2

6.85 g (50 mmol) of salicylic acid amide are added, dropwise, to 11.5 ml of benzoyl chloride and the mixture is heated to 170° C. The mixture is then stirred for 30 minutes at this temperature. During this time, the salicylic acid dissolves to produce, on cooling, a honey-like mass which is then stirred with diethyl ether to yield a white solid which is filtered off, washed with diethyl ether and dried. There are obtained 8.78g of 2-phenyl-4H-1,3-benzoxazin-4-one as a white powder melting at 104–105° C. and having the following elemental analysis:

$C_{14}H_9NO_2$ requires: C 75.33%; H 4.06%; N 6.29% Found: C 74.82%; H 4.09%; N 6.15%

EXAMPLE 3

6.85 g (50 mmol) of salicylic acid amide are added, dropwise, to 18.1 g of p-methoxybenzoyl chloride and the mixture is heated to 150° C. The mixture is then stirred for 30 minutes at this temperature. After cooling, the honey-like mass is stirred with 100 ml of isopropanol, the precipitated solid filtered off and dried to yield 10.2 g of 2-(4-methoxyphenyl)-4H-1,3-benzoxazin-4-one as a white solid melting at 175–178° C. and having the following elemental analysis:

$C_{15}H_{11}NO_3$ requires: C 71.14%; H 4.38%; N 5.53%; O 18.95% Found C 70.94%; H 4.43%; N 5.42%; O 18.99%.

If the honey-like mass is treated with benzamidine hydrochloride, as described in the second step of Example 1, there are obtained 15.82 g of 2-(4-methoxyphenyl)-4-hydroxyphenyl-6-phenyl-1,3,5-triazine melting at 177–178° C. and having the following elemental analysis:

$C_{22}H_{17}N_3O_2$ requires: C 74.35%; H 4.82%; N 11.82% Found C 74.5%; H 4.9%; N 11.9%.

EXAMPLE 4

36.6 g of 4-nitrobenzoyl chloride are added to 48 g of p-xylene over 5 minutes and the suspension warmed to 80° C. To this suspension is then added, over 90 minutes, at 80° C., a solution of 13.2 g of salicylic acid amide in 7.2 g of dimethylacetamide, with stirring. The temperature is then raised to 135° C. over 1 hour and the mixture stirred at this temperature for a further 6 hours. After this time, the mixture is treated with 48 g of p-xylene, cooled to 80° C., the precipitated solids filtered, washed with p-xylene and dried, to yield 25.87 g of 2-(4-nitrophenyl)-4H-1,3-benzoxazin-4-one melting at 249–251° C. and having the following elemental analysis:

$C_{14}H_8N_2O_4$ requires: C 62.69%; H 3.01%; N 10.44% Found C 61.38%; H 3.08%; N 10.26%.

Treatment of this product With benzamidine hydrochloride, as described in the second step of Example 1, yields 28.9 g of 2-(4-nitrophenyl)-4-hydroxyphenyl-6-phenyl-1,3,5-triazine, melting at 238–240° C. and having the following elemental analysis:

$C_{21}H_{14}N_4O_3$ requires: C 68.10%; H 3.81%; N 15.13%; O 12.96% Found C 68.25%; H 3.89%; N 15.10%; O 12.76%.

What is claimed is:

1. A process for the production of a 1,3-benzoxazin-4-one having the formula.

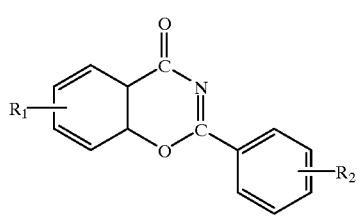

(1)

in which $R_1$ and $R_2$, independently, are hydrogen, cyano, halogen, nitro, $C_1$–$C_{20}$alkyl, O—$C_1$–$C_{20}$alkyl, phenyl, NH—CO—$C_1$–$C_{20}$alkyl, $N(R_3)_2$, $SO_2N(R_3)_2$, $COOR_3$ or $CON(R_3)_2$ in which $R_3$ is hydrogen, cyano, halogen, nitro, $C_1$–$C_{20}$alkyl, O—$C_1$–$C_{20}$alkyl, phenyl or NH—CO—$C_1$–$C_{20}$alkyl, comprising reacting, at elevated temperature, 1 molar equivalent of an o-hydroxybenzamide of the formula:

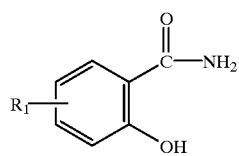

(2)

in which $R_1$ has its previous significance, with 2 to 6 molar equivalents of a benzoyl chloride of the formula:

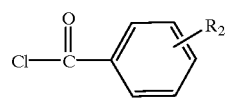

(3)

in which $R_2$ has its previous significance, in which the process is conducted by heating the reaction mixture, in the absence of any external solvent, until a melt is formed, using a molar ratio of the reactant of formula (3) to the reactant of formula (2) ranging from 2.01:1 to 4:1.

2. A process according to claim 1 in which a compound of formula (2) is used in which $R_1$ is hydrogen, cyano, chloro, nitro, $C_1$–$C_4$alkyl, $C_1$–$C_4$alkoxy, NH—CO—$C_1$–$C_4$alkyl, $N(C_1$–$C_4$alkyl$)_2$, $SO_2N(C_1$–$C_4$alkyl$)_2$, CON$(C_1$–$C_4$alkyl$)_2$, CO—O$C_1$–$C_4$alkyl or phenyl.

3. A process according to claim 1 or 2 in which a compound of formula (3) is used in which $R_2$ is hydrogen, cyano, chloro, nitro, $C_1$–$C_4$alkyl, $C_1$–$C_4$alkoxy, NH—CO—$C_1$–$C_4$alkyl, $N(C_1$–$C_4$alkyl$)_2$, $SO_2N(C_1$–$C_4$alkyl$)_2$, CON$(C_1$–$C_4$alkyl$)_2$, CO—O$C_1$–$C_4$alkyl or phenyl.

4. A process according to claim 1 in which the process is conducted at a temperature ranging from 50° C. to 180° C.

5. A process according to claim 4 in which the process is conducted at a temperature ranging from 100° C. to 140° C.

6. A process according to claim 1 in which the process is carried out over a reaction time within the range of from 1 to 24 hours.

7. A process according to claim 6 in which the process is carried out over a reaction time within the range of from 2 to 5 hours.

8. A process according to claim 1 in which the process is conducted using a molar ratio of the reactant of formula (3) to the reactant of formula (2) ranging from 2.01:1 to 2.5:1.

9. A process according to claim 1 in which the reactant of formula (2) is 2-hydroxy-, 2-hydroxy-4-cyano-, 2-hydroxy-4-chloro-, 2-hydroxy-5-nitro-, 2-hydroxy-4-methyl-, 2-hydroxy-5-ethyl-, 2-hydroxy-4-methoxy-, 2-hydroxy-4-ethoxy-, 2-hydroxy-4-methoxycarbonylamino-, 2-hydroxy-5-butoxycarbonylamino-, 2-hydroxy-4-dimethylamino-, 2-hydroxy-5-diethylamino-, 2-hydroxy-4-dimethylaminosulfonyl-, 2-hydroxy-4-dibutylaminosulfonyl-, 2-hydroxy-dimethylaminocarbonyl-, 2-hydroxy-5-dipropylaminocarbonyl-, 2-hydroxy-4-methoxycarbonyl-, 2-hydroxy-3-ethoxycarbonyl- or 2-hydroxy-4-phenyl-benzamide.

10. A process according to claim 1 in which the reactant of formula (3) is benzoic acid chloride, 4-cyano-, 4-chloro-, 4-nitro- 5-nitro-, 4-methyl-, 5-ethyl-, 4-methoxy-, 4-ethoxy-, 4-methoxycarbonylamino-, 5-butoxycarbonylamino-, 4-dimethylamino-, 5-diethylamino-, 4-dimethylaminosulfonyl-, 4-dibutylaminosulfonyl-, dimethylaminocarbonyl-, 5-dipropylaminocarbonyl-, 4-methoxycarbonyl-, 3-ethoxycarbonyl- or 4-phenyl-benzoic acid chloride.

* * * * *